US012089885B2

(12) United States Patent
Haziza

(10) Patent No.: US 12,089,885 B2
(45) Date of Patent: Sep. 17, 2024

(54) K-WIRE DEPTH MEASUREMENT

(71) Applicant: Premia Spine Ltd., Ramat Poleg (IL)

(72) Inventor: Rafi Haziza, Kiryat Bialik (IL)

(73) Assignee: Premia Spine Ltd., Ramat Poleg (IL)

( * ) Notice: Subject to any disclaimer, the term of this patent is extended or adjusted under 35 U.S.C. 154(b) by 977 days.

(21) Appl. No.: 17/046,783

(22) PCT Filed: Apr. 7, 2019

(86) PCT No.: PCT/IB2019/052849
§ 371 (c)(1),
(2) Date: Oct. 11, 2020

(87) PCT Pub. No.: WO2019/197957
PCT Pub. Date: Oct. 17, 2019

(65) Prior Publication Data
US 2021/0161571 A1 Jun. 3, 2021

Related U.S. Application Data

(60) Provisional application No. 62/656,492, filed on Apr. 12, 2018.

(51) Int. Cl.
*A61B 17/84* (2006.01)
*A61B 17/16* (2006.01)
(Continued)

(52) U.S. Cl.
CPC ........ *A61B 17/848* (2013.01); *A61B 17/3472* (2013.01); *A61B 17/8897* (2013.01);
(Continued)

(58) Field of Classification Search
CPC .............. A61B 17/848; A61B 17/3472; A61B 17/8897; A61B 17/15; A61B 17/1697;
(Continued)

(56) References Cited

U.S. PATENT DOCUMENTS 5,180,388 A * 1/1993 DiCarlo ................. A61B 17/17
606/104
5,895,389 A * 4/1999 Schenk ................. A61B 17/17
606/80

(Continued)

FOREIGN PATENT DOCUMENTS

WO 2016/166662 10/2016

OTHER PUBLICATIONS

PCT Search Report and Written Opinion PCT/IB2019/052849, Jul. 19, 2019.

*Primary Examiner* — Marcela I. Shirsat
(74) *Attorney, Agent, or Firm* — Dekel Patent Ltd; David Klein

(57) ABSTRACT

An assembly includes a surgical device (10) including a distal interface member (12) and a proximal handle (14), the distal interface member (12) including a connecting element (16) for connecting to a surgical tool (18), and a K-wire (20) that passes through a central passageway of the surgical device (10) distally through the distal interface member (12) into a lumen of the surgical tool (18). A wire depth measurement tool (30) includes a handle interface member (32) that assembles to the handle (14) and one or more graduated scales (36) that extend proximally from the handle interface member (32). The graduated scales (36) include depth graduations for indicating an amount a tip of the K-wire (20) protrudes from a distal end of the surgical tool (18).

6 Claims, 2 Drawing Sheets

(51) Int. Cl.
*A61B 17/34* (2006.01)
*A61B 17/70* (2006.01)
*A61B 17/88* (2006.01)
*A61B 90/00* (2016.01)

(52) U.S. Cl.
CPC .......... *A61B 90/06* (2016.02); *A61B 17/1697* (2013.01); *A61B 17/7092* (2013.01); *A61B 2090/062* (2016.02); *B23B 2251/52* (2013.01); *B23B 2260/0485* (2013.01); *B25D 2250/055* (2013.01); *Y10T 83/921* (2015.04); *Y10T 83/925* (2015.04); *Y10T 408/8925* (2015.01)

(58) Field of Classification Search
CPC ... A61B 17/17; A61B 17/171; A61B 17/1717; A61B 17/1796; A61B 17/7092; A61B 17/1626; A61B 90/06; A61B 2290/062; B23B 49/005; B23B 49/003; B23B 2260/0485; B23B 2251/52; B25D 2250/055; Y10T 408/8925; Y10T 83/921; Y10T 83/925; B23Q 17/0923

USPC ........................................................ 606/102
See application file for complete search history.

(56) References Cited

U.S. PATENT DOCUMENTS

| | | | |
|---|---|---|---|
| 2009/0157077 A1 | 6/2009 | Larsen | |
| 2009/0228015 A1* | 9/2009 | Ellis | A61B 5/1076 606/86 R |
| 2010/0145340 A1* | 6/2010 | Phan | A61B 17/3417 606/104 |
| 2013/0096565 A1* | 4/2013 | Fritzinger | A61B 90/06 606/102 |
| 2014/0276884 A1* | 9/2014 | Lizardi | A61B 90/00 606/102 |
| 2014/0296861 A1* | 10/2014 | McCarthy | A61B 90/06 606/96 |
| 2016/0030106 A1 | 2/2016 | Carter | |
| 2016/0250039 A1 | 9/2016 | Chow | |

* cited by examiner

K-WIRE DEPTH MEASUREMENT

FIELD OF THE INVENTION

The present invention relates generally to methods and apparatus for measuring depth of a Kirschner wire (K-wire) that passes through a surgical tool, such as but not limited to, screwdrivers, taps, bores, awls, probes, jamshidi needles, and others.

BACKGROUND OF THE INVENTION

For example, in certain surgical procedures, a K-wire or similar guide wire (the terms being used interchangeably throughout) is used in combination with a cannulated surgical tool, such as a screwdriver, tap, bore, awl, probe, or jamshidi needle, to name some. The K-wire is positioned through the pedicle and into the vertebral body to indicate or establish the position of subsequent screw placement. Once the proper positioning of the K-wire is confirmed by X-rays, the screw connected to the screwdriver is guided over the K-wire through the lumen (cannula) of the surgical tool and penetrates into the bone, which if not done properly can injure the patient, particularly if the K-wire encounters certain sensitive tissues. The procedures often require the use of force which can cause an otherwise properly positioned K-wire to move forward into the surgical site, which if excessive can move into contact where contact is to be avoided.

Measurement of the depth of the K-wire, that is, the amount the tip of the K-wire protrudes from the distal end of the surgical tool, is critical for patient safety. In a normal screw placement over a K-wire, the K-wire is placed to the desired depth, and then the screw is advanced over the K-wire. The surgeon must make sure the tip of the K-wire is not pushed further distally towards the anterior cortex of the vertebral body. If the K-wire tip were to puncture through the vertebra it could damage major blood vessels and cause major bleeding.

SUMMARY OF THE INVENTION

The present invention seeks to provide an improved device for measuring the depth of a K-wire, as described more in detail hereinbelow.

The term K-wire throughout the specification and claims encompasses any slender, elongated piece with a tip used for entering bone, such as a K-wire or Steinmann pin or guidewire.

There is thus provided in accordance with an embodiment of the present invention an assembly including a surgical device including a distal interface member and a proximal handle, the distal interface member including a connecting element for connecting to a surgical tool, and a K-wire that passes through a central passageway of the surgical device distally through the distal interface member into a lumen of the surgical tool, and a wire depth measurement tool that includes a handle interface member that assembles to the handle and one or more graduated scales that extend proximally from the handle interface member, the one or more graduated scales including depth graduations for indicating an amount a tip of the K-wire protrudes from a distal end of the surgical tool.

In accordance with an embodiment of the present invention the handle interface member includes a threaded connection and a knob, wherein the threaded connection mates with the handle and is tightened or loosened by turning the knob.

In accordance with an embodiment of the present invention the K-wire is locked in place in the handle by means of a locking element.

In accordance with an embodiment of the present invention the one or more graduated scales include a plurality of scales that face different directions.

In accordance with an embodiment of the present invention the wire depth measurement tool is formed with a lumen for the K-wire to pass through.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
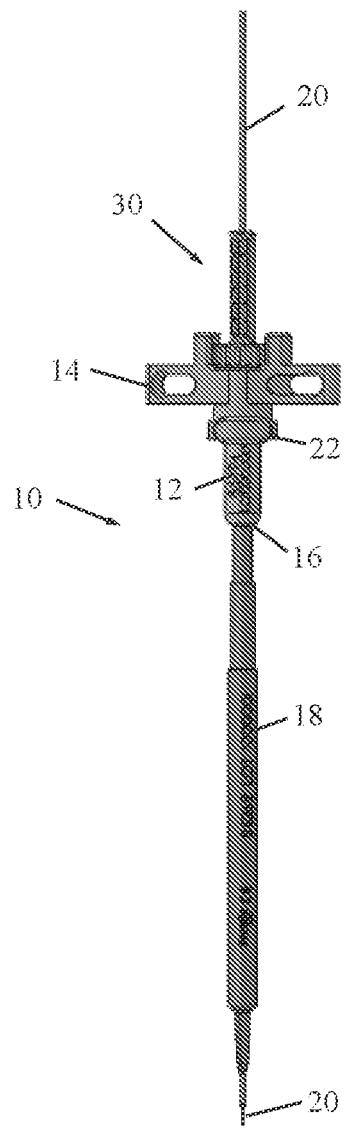
FIG. 1 is a simplified illustration of a surgical tool assembled with a wire depth measurement tool, constructed and operative in accordance with an embodiment of the present invention.
Figure 2:
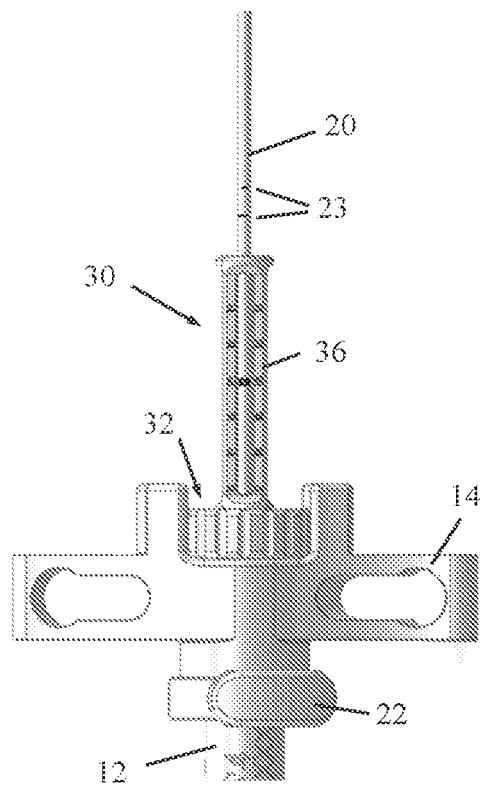
FIG. 2 is a simplified illustration of the wire depth measurement tool assembled on a handle of the surgical tool.
Figure 5:
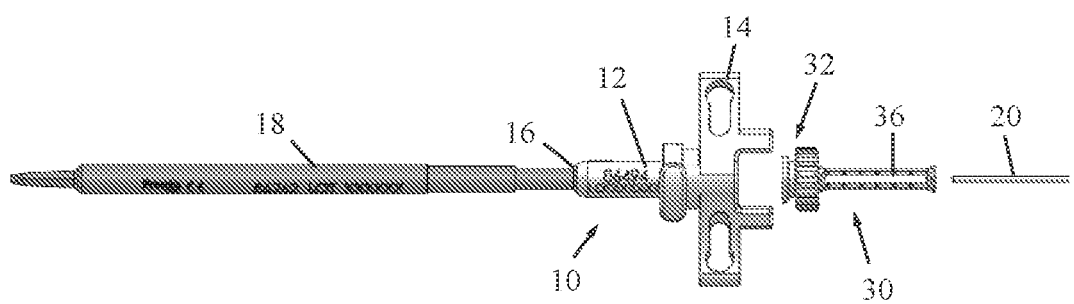
FIG. 5 is a simplified exploded illustration of the surgical tool, wire depth measurement tool and K-wire.

Reference is now made to FIGS. 1-2 and 5, which illustrate a surgical device 10 assembled with a wire depth measurement tool 30, constructed and operative in accordance with a non-limiting embodiment of the present invention.

Surgical device 10 may be, but not necessarily, constructed similarly to the tool described in PCT Patent Application PCT/IB2016/052074 (WO 2016/166662).

Surgical device 10 includes a distal interface member 12 and a proximal handle 14. Distal interface member 12 includes a connecting element 16 for connecting to a surgical tool 18, such as but not limited to, a cannulated pedicle awl, a screw, a screwdriver, a tap, a bore, a probe, or a jamshidi needle and the like. For example, connecting element 16 may be a quick-disconnect connector that secures to the proximal end of tool 18. Surgical device 10 is formed with a central passageway or lumen formed through distal interface member 12 and handle 14, and through surgical tool 18. Two or more surgical tools may be connected to each other, such as a screwdriver connected to a pedicle screw.

A K-wire 20 passes through the central passageway of surgical device 10 distally through distal interface member 12 into the lumen of surgical tool 18, and then can pass distally out the distal tip of surgical tool 18. The K-wire 20 may be locked in place in the handle 14 by means of a locking element 22 (such as, but not limited to, a screw or nut).

Figure 3:
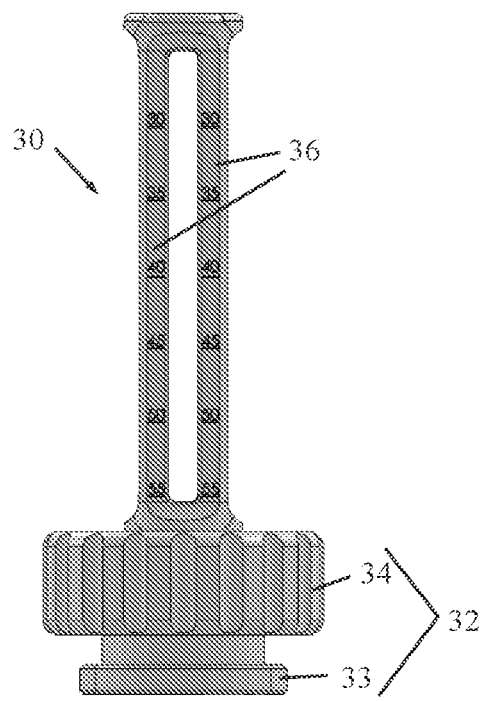
FIGS. 3 and 4 are simplified plan-view and perspective illustrations, respectively, of the wire depth measurement tool, in accordance with a non-limiting embodiment of the present invention.
Figure 4:
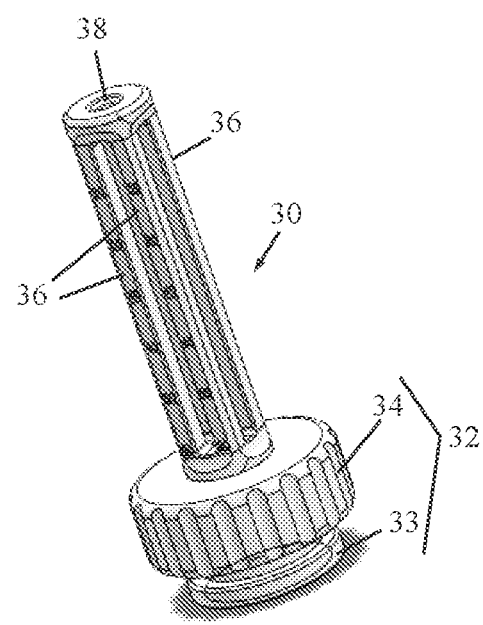

The wire depth measurement tool 30, shown particularly in FIGS. 3 and 4, includes a handle interface member 32 that assembles to the handle 14. For example, handle interface member 32 may include a threaded connection 33 and a knob 34. The male (or female) threaded connection 33 mates with a corresponding (female or male) threaded portion of handle 14 and is tightened or loosened by turning knob 34 in the appropriate direction. Alternatively, handle interface member 32 may connect to handle 14 or even to surgical tool 18 by other means, such as but not limited to, quick disconnect connections, press fit, snap fit, bayonet connections and others.

One or more graduated scales 36 extend proximally from handle interface member 32. Each graduated scale 36 has depth graduations for indicating the depth of K-wire 20, that is, the amount the tip of K-wire 20 protrudes from the distal end of the surgical tool 18. There are preferably several graduate scales 36 that face different directions so the surgeon can easily see the depth graduations at any viewing angle. The wire depth measurement tool 30 is formed with a lumen 38 for the K-wire 20 to pass through. The wire depth measurement tool 30 is pre-calibrated such that when tool 30 is properly assembled on surgical device 10, the graduated scale 36 accurately indicates the depth of K-wire 20.

In another aspect of the invention, K-wire 20 includes one or more depth graduations 23, which may be laser marked, etched or otherwise disposed at least partially around the circumference of K-wire 20.

What is claimed is:

1. An assembly comprising:
   a surgical device comprising a distal interface member and a proximal handle, said distal interface member comprising a connecting element for connecting to a surgical tool, and a K-wire that passes through a central passageway of said surgical device distally through said distal interface member into a lumen of said surgical tool; and
   a wire depth measurement tool that comprises a handle interface member that assembles to said handle and graduated scales that extend proximally from, and are affixed to, said handle interface member, said graduated scales comprising depth graduations for indicating an amount a tip of said K-wire protrudes from a distal end of said surgical tool, and said graduated scales being separated from each other by a longitudinal gap that extends along a length of each of said graduated scales, and said K-wire extends at least partially through said longitudinal gap.

2. The assembly according to claim 1, wherein said handle interface member comprises a threaded connection and a knob, wherein said threaded connection mates with said handle and is tightened or loosened by turning said knob, and wherein said graduated scales are coupled to, and extend perpendicularly outwards from, one side of said knob.

3. The assembly according to claim 1, wherein said K-wire is locked in place in said handle by means of a locking element.

4. The assembly according to claim 1, wherein said graduated scales comprise a plurality of scales that face different directions.

5. The assembly according to claim 1, wherein said wire depth measurement tool is formed with a lumen for said K-wire to pass through.

6. The assembly according to claim 1, wherein said K-wire comprises one or more depth graduations disposed at least partially around a circumference of said K-wire.

* * * * *